United States Patent [19]

McAnalley et al.

[11] Patent Number: 5,284,833
[45] Date of Patent: Feb. 8, 1994

[54] WOUND CLEANSER

[75] Inventors: Bill H. McAnalley, Grand Prairie; D. Eric Moore, Richardson, both of Tex.

[73] Assignee: Carrington Laboratories, Inc., Irving, Tex.

[21] Appl. No.: 975,893

[22] Filed: Nov. 13, 1992

Related U.S. Application Data

[63] Continuation of Ser. No. 720,253, Jun. 24, 1991, abandoned.

[51] Int. Cl.$^5$ .................. A01N 43/04; A61K 31/715; A61K 37/12; A61K 35/14
[52] U.S. Cl. .................................... 514/23; 514/54; 514/55; 514/53; 514/21; 514/846; 514/60; 424/543; 424/549
[58] Field of Search .............. 514/23, 54, 55, 57, 514/53, 21, 846, 191, 60; 424/543, 549

[56] References Cited

U.S. PATENT DOCUMENTS

| | | | |
|---|---|---|---|
| 3,812,252 | 5/1974 | Silvetti | 514/60 |
| 4,401,651 | 8/1983 | Knutson | 514/53 |
| 4,708,873 | 11/1987 | Schulte | 424/195.1 |
| 4,801,451 | 1/1989 | Hellgren et al. | 424/94 |
| 4,822,601 | 4/1989 | Goode et al. | 514/54 |
| 4,839,080 | 6/1989 | Jungermann et al. | 514/54 |
| 4,859,656 | 8/1989 | Kjelleberg et al. | 514/54 |
| 4,963,491 | 10/1990 | Hellgren et al. | 435/264 |
| 4,970,220 | 11/1990 | Chaussee | 514/846 |
| 5,047,249 | 9/1991 | Rothman et al. | 514/21 |

FOREIGN PATENT DOCUMENTS

| | | |
|---|---|---|
| 431884 | 6/1991 | European Pat. Off. |
| 2267112 | 7/1975 | France |

OTHER PUBLICATIONS

R. Dolder and S. Skinner (Editors) Opthalmika, 1983, pp. 392-415.
Lancet, vol. 2, No. 8456, Sep. 21, 1985, pp. 663-665, H. Gordon, et al. Sugar and Wound Healing.
Antimicrobial Agents in Chemotherapy, vol. 35, No. 1, pp. 24-28 1991, I. Gruda, et al.
Journal of Toxicology Clinique Et Experimentale, vol. 10, No. 3, p. 205, Jun. 1990, M. Cornelis, et al.
Pharmacology & Therapeutics in Dentistry, vol. 6, No. 3-4, pp. 99-107, 1981, C. M. Wernette, et al.
George Rodeheaver, Ph.D., "Controversies in Topical Wound Management", Premier Issue, Apr. 1989, pp. 19-27.
Richard F. Edlich, et al., "Technical Factors in the Prevention of Wound Infections", Chapter 19, Second Edition, Surgical Infectious Diseases, pp. 331-350.
F. M. Tatnall, et al., "Comparative Study of Antiseptic Toxicity on Basal Keratinocytes, Transformed Human Keratinocytes and Fibroblasts", Skin Pharmacol 1990; 3:157-163.
S. S. Brennan, et al., "The effect of antiseptics on the healing wound: a study using the rabbit ear chamber", Br. J. Surg. 1985, vol. 72, Oct., 780-782.
Diane Krasner, RN, MS, CETN, "Appendix 1", Chronic Wound Care: A Clinical Source Book for Healthcare Professionals, Apr. 1990, pp. 470-474.

*Primary Examiner*—Michael G. Wityshyn
*Assistant Examiner*—Louise N. Leary
*Attorney, Agent, or Firm*—Winstead Sechrest & Minick

[57] ABSTRACT

Rationally designed wound cleanser that is physiologically compatible. The wound cleanser comprises a surfactant, an osmotic adjuster, a buffering agent, and water. The composition may also contain a preservative, a sudsing agent, a skin protectant, a pH adjuster, and a stabilizer.

50 Claims, 1 Drawing Sheet

WOUND CLEANSER

This is a continuation of application Ser. No. 07/720,253, filed Jun. 24, 1991, now abandoned.

BACKGROUND OF THE INVENTION

This invention relates to wound cleansing compositions, and particularly to physiologically compatible wound cleansing compositions and wound cleansing concentrates.

Emergency room physicians treat an estimated ten million traumatic wounds each year in the United States. The goal in treating these wounds is to prevent infection, restore function and provide good cosmoses.

Wound healing has been the subject of trials and errors for thousands of years. In treating wounds, people have tried mud packs, honey poultices, fire, dry and moist dressings. Only recently, however, has the underlying molecular process of wound healing been extensively studied. One finding has been that a handful of growth factors play key roles in every step of wound healing—from the response immediately following an injury to bringing the healing process to an orderly close. Another component in would healing is the extracellular matrix. This matrix is a cross-linked structure of proteins and polysaccharides, whose structure organizes the geometry of normal tissue. It is the delicate balance between growth factors and the matrix that is important in every step of wound healing.

Following a cut, fibrinogen, which is a protein circulation in the blood stream, forms a fibrin clot, sealing damaged blood vessels. Fibronectin, another protein in the clot, links up to the matrix, forming a bridge between the clot and the surrounding tissue.

The matrix, however, does more than simply stabilize the clot. Alterations in the matrix caused by injury appear to initiate cellular response, including the release of growth factors. For example, before wounding, basic fibroblast growth factor (bFGF) is tightly bound to the matrix outside normal skin and muscle cells, and probes for the bFGF receptor on the cells' surfaces or for its messenger RNA inside them come up negative.

Soon after any major invasive insult, either a mechanical or chemical injury, this picture changes dramatically. The matrix releases bFGF and signals cells to begin manufacturing that growth factor and expressing its receptor on their surface. Each of the growth factors produced during wound healing causes a variety of cell types to proliferate. Unless the growth factors are confined to the wound, they could stimulate cell division where it is not needed and could actually be harmful. It is the matrix that choreographs this healing process. The matrix functions as a combination "passageway and road sign" system, guiding rapidly moving cells toward the target zone. Thus the cell firs breaks free from its initial position in the matrix, then moves along the matrix toward the wound, and eventually anchors itself again.

For a wound to heal with maximum efficiency, proper cleansing is essential. The purpose of wound cleansing in the management of a wound is to prevent infection and to promote healing of the injured tissue. Wound cleansing is accomplished by removal of contaminating bacteria and debridement of necrotic tissue and foreign materials from the wound.

Wound cleansing and wound disinfection have often been combined. Thus, most manufacturers of wound cleansers have traditionally added some antiseptic reagent, in excess of what is actually needed, to their would cleansing materials. Technically, wound cleansing and would disinfection are two areas of wound management that should be considered as separate components. Each component has a specific purpose. It is acceptable to cleanse the wound first and then, if needed, to disinfect it with an appropriate antiseptic material. Excess disinfectants, regardless of type, cause damage to a tissue and will interfere with tissue function, thus they increase the injury that already exists and, consequently, delay wound healing. The inappropriateness of adding excess disinfectant to a would cleanser is shown by the fact that a wound has an exquisite capability to protect itself against bacterial challenges if its natural defenses are not inhibited.

Cells that are important to wound healing include: (1) Fibroblasts that are going to result in the healing; and (2) the granulocytes and monocytes that are going to clean up and eliminate the bacteria and foreign debris. The monocytes/macrophage system orchestrates all phases of wound healing.

In the management of a wound, one should strive to avoid adding trauma to the injured tissues. By definition, a would is either a physical or a chemical trauma to the body. A wound is a traumatic insult to the integrity of a tissue. Thus, any additional trauma inflicted upon the tissue would simply delay the healing process.

Mechanical trauma is any physical force applied to a tissue and which physical force exceeds the physiological limits of the tissue. Thus, physical trauma includes additional trauma that one imparts to the wound in over zealous attempts to cleanse it by scrubbing with an abrasive material, or the inappropriate removal of adherent dressings.

Chemical trauma occurs when a physiologically incompatible agent is added to a tissue. Thus, chemical trauma includes any non-physiological agent added to a wound.

Commercial wound cleansers consist principally of two parts: An active agent and a carrier. The active ingredients generally possess surface active effects. Unfortunately, the carriers used in many of the commercially available wound cleansers are toxic. Consequently, although the active agents may have physiologic benefits, they do not normally transfer that benefit to the wound because of their innate toxicity and toxicity associated with the carrier. Most commercial products do not balance their efficacy and safety physiochemical profile.

Dakin's solution, a buffered 0.5 percent solution of sodium or potassium hypochlorite, was introduced in World War I as an antiseptic irrigant for a wound. It is now known to be injurious to tissues, and is therefore considered more a debriding agent than a cleansing one. Its antimicrobial action is due to release of hypochlorous acid, which is active in neutral or acidic solutions but is less active in alkaline solutions.

Dilute solutions of quaternary ammonium salts are cationic surface-active agents used to cleanse wounds. But these solutions have the drawback of being effective only on gram-positive microorganisms.

Another cleanser is topical iodophor. The combination of iodine and a solubilizing agent slowly liberates free iodine when diluted with water, and is therefore called an iodophor (iodo-iodine, and phor-carrier). Application of iodophor over large wound surfaces usually results in a substantial increase in free iodine. However, included in the complications of iodophor absorptions are renal failure, metabolic acidosis, and increased serum enzyme levels. One example of iodophor is Betadine ® (Purdue Frederick). It is a surgical scrub solution containing 7.5 percent polyvinylpyrrolidone-iodine with 0.75 percent free iodine and an anionic detergent.

Hydrogen peroxide is commonly used as a wound irrigant. It has little value as an antiseptic and is more effective as a sporicide than a bactericide. However, even low concentrations of hydrogen peroxide are damaging to tissues.

Chlorohexidine is used as a wound irrigant solution because of its antimicrobial activity. Although it has good antibacterial properties, a 0.5 percent solution of chlorhexidine has been found to slow granulation issue formation with prolonged wound contact.

PHisoHex ® (Withrop Laboratories) is an antibacterial sudsing emulsion. It contains a colloidal dispersion of 3 percent (w/v) hexachlorophene in an emulsion consisting of entsufon sodium, petrolatum, lanolin cholesterols, methylcellulose, polyethylene glycol, polyethylene glycol monostearate, lauryl myristyl diethanolamide, sodium benzoate and water. Entsufon sodium, or sodium octylphenoxy-ethoxyethyl ether sulfonate, is a synthetic detergent. Hexachlorophene is active against Gram-positive bacteria, but its effect on Gram-negative bacteria is weak.

Hibiclens ® (Stuart Pharmaceuticals) contains 4 percent chlorhexidine gluconate and 4 percent isopropyl alcohol in a mild sudsing base (poloxamer) adjusted to pH 5.0 to 6.5. Further, it also contains a fragrance. It has activities against both Gram-positive and Gram-negative bacteria.

Shur-Clens ® ()Biosyntec, Inc.) is a skin wound cleanser that has been approved by the Food and Drug Administration for use in man. It contains about 20 percent polyoxamer 188. This polyol contains 80 percent ethylene oxide content by weight with an average molecular weight of 8,350. It is a nonionic detergent that does not display antibacterial activity.

Pluronic F-68 (BASF Wyandotte Corp.) is a new skin wound cleanser that has also been approved by the Food and Drug Administration for use in man. It is a surface-active agent that solubilizes iodine resulting in a Pluronic iodophor. Pluronic F-68 is synthesized by adding propylene oxide to the two hydroxyl groups of a propylene glycol nucleus. To the ends of this hydrophobic base are added hydrophilic ethylene oxide units. In the case of Pluronic F-68, the hydrophilic groups are controlled in length to constitute 80 percent of the final molecule.

U.S. Pat. No. 4,708,873 to Schulte describes a composition adapted for application to the skin consisting of a solution of biphenamine in aloe vera. The solution is used to promote debridement of necrotic tissue from an abnormal, ulcerated necrotic tissue on sin or mucous membrane of a patient. It is claimed that the biphenamine is being dissolved in aloe vera to promote healing of the lesion.

In the management of a wound, one saying to consider is; "Do not put in a wound what you would not put in your own eye."

Desirable characteristics of a wound cleanser include that it must not break down local or systemic defenses, and that it must not interfere with the natural wound healing process. Further, the indications and method of application are also of importance. Thus, in the cleaning of a fresh, heavily contaminated wound, the method of application is more important than the type of solution. whereas the reverse is true in cleansing an already infected wound where the cleanser is an aid in debridement.

It is seen that most of the commercially available wound cleansers are either toxic or not physiologically compatible. Further, many of the rather exotic wound cleansers are rather expensive. The present invention overcomes many of the prior art problems as discussed above.

SUMMARY OF THE INVENTION

It is thus advantageous, and this is one object of this invention, to obtain a non-toxic and physiologically compatible wound cleanser either in an aqueous form or in a concentrate from that can be constituted with water to give the final aqueous wound cleanser.

It is another object of the present invention to provide a wound cleanser that will minimize the disturbance of wound healing.

It is still another object of the present invention o provide a wound cleanser that not only will clean the wound ut also promote the healing of the wound.

It is yet another object of the present invention to provide a wound cleanser that: (1) Is physiologically compatible to the living tissue; (2) causes minimal damage to the living tissue; (3) has low surface tension; (4) is non-irritating to the living tissue; (5) passes the eye-sensitivity test; (6) has mild antibacterial activities; (7) has mild antifungal activities; (8) has mild antimycotic activities; (9) passes the preservative test for "multiple" uses; and (10) is relatively inexpensive.

Figure 1:
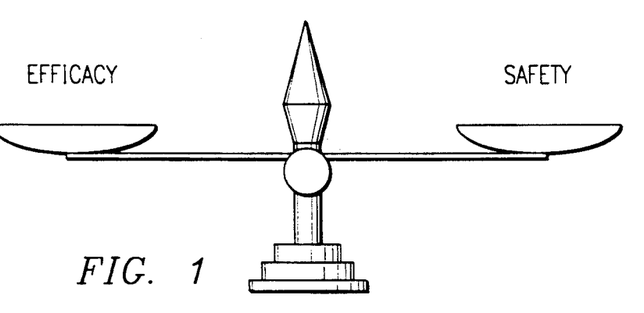
FIG. 1 shows the general goals to be achieved from the rational design of the present invention.

In short, a general object of the present invention is to provide a wound cleanser that has a proper balance of efficacy and safety physiochemical profile. (FIG. 1.) The efficacy criteria includes antimycotic, antibacterial, lower surface tension, and passing preservative challenge tests. For safety purposes, the wound cleanser must pass dermal sensitivity tests and eye sensitivity tests.

Broadly, the aqueous wound cleanser according to the invention comprises, on a weight percent basis, from about 0.01 percent to about 50 percent of a surfactant to give the composition a surface tension of below about 30 dynes/cm; from about 0.05 percent to about 10 percent of an osmotic adjuster to give the composition an osmolality of from about 200 to about 320 mOs/liter; from about 0.05 percent to about 3 percent of a buffer to maintain a pH in a range of from about 6 to about 7.7 in the composition; and a sufficient amount of water necessary to establish the foregoing properties.

The concentrated mixture is suitable for re-constituting with water to form a final aqueous wound cleanser which comprises, on a weight percent basis based on the weight of the final aqueous wound cleanser, from about 0.01 percent to about 50 percent of a neutral surfactant; from about 0.05 percent to about 10 percent of an osmotic adjuster; and from about 0.05 percent to about 3 percent of a buffering agent. Further, when the concentrated mixture is constituted with water to give the final aqueous wound cleanser that is physiologically compatible and having the weight percents listed above, this final aqueous wound cleanser has a surface tension of below about 30 dynes/cm, an osmolality of from about 200 to about 230 mOs/liter, and a pH in the range of from about 6 to about 7.7. The concentrated mixture could be in the form of either a thick liquid or an essentially dry mixture.

The present invention is rationally designed based on a number of new discoveries and combination of such discoveries with known scientific data which are summarized below:

(1) A fundamental tenet in the management of traumatic wounds, or soft tissue injuries, involves successful wound cleansing.

(2) The main function of a wound cleanser is to cleanse the wound which may be contaminated by exudate, bacteria, mold, fungus, necrotic debris, blood clots, dirt, and eschar.

(3) In order for cleansing to occur, dispersive activity effects must occur. The bond between the foreign body and the wound tissue must be broken and the interfacial tension must be reduced so that the foreign body can be rinsed out of the wound.

(4) A surfactant, or surface active agent, reduces the surface tension between the contaminants and the wound surface, thereby facilitating their removal from the wound surface. In addition, a surfactant solubilizes relatively insoluble particles thus encouraging their dislodgment from the wound surface.

(5) A surfactant is an effective wound cleanser.

(6) A desirable wound cleanser should be nontoxic, noncytotoxic, and nonsensitizing.

(7) Selected nonionic surfactants, as compared to those having a full chemical charge, are relatively safe and nontoxic.

(8) Potassium ion induces depolarization of the nerve and causes pain. Thus, as a rule, a solution containing sodium ions is less painful to the patient than a solution containing potassium ions.

(9) A desirable wound cleanser should be biocompatible and physiologically compatible with the body tissue, thus able to bring about a natural recovery from the injury.

(10) Biocompatibility in a wound cleanser depends, among other factors, upon: Proper pH of the cleanser (preferably around the physiological pH); osmolarity of the cleanser (preferably isotonic); types of ions present in the cleanser (sodium is preferred over potassium); polarity (preferably polar); and charges (preferably nonionic).

(11) Any agents that damage tissue and interfere with tissue function increase the injury that already exists and delay wound healing.

(12) Proper amounts and types of preservatives are needed in a wound cleanser for it to pass the preservative challenge test.

(13) A wound heals better in a slightly acidic condition than in a basic condition.

(14) A physiological pH is beneficial to the in vitro growth of keratinocytes and could help in wound healing.

(15) For wounds to heal faster, it is best to keep them clean and moist.

(16) Mannitol is a moisturizing agent. Microorganisms do not readily digest mannitol as they do other saccharides.

(17) Dissolved mannitol can change tonicity of the solution.

(18) Best cleansing technique is gentle irrigation with copious quantities of water or specific nonionic surfactants.

Figure 2:
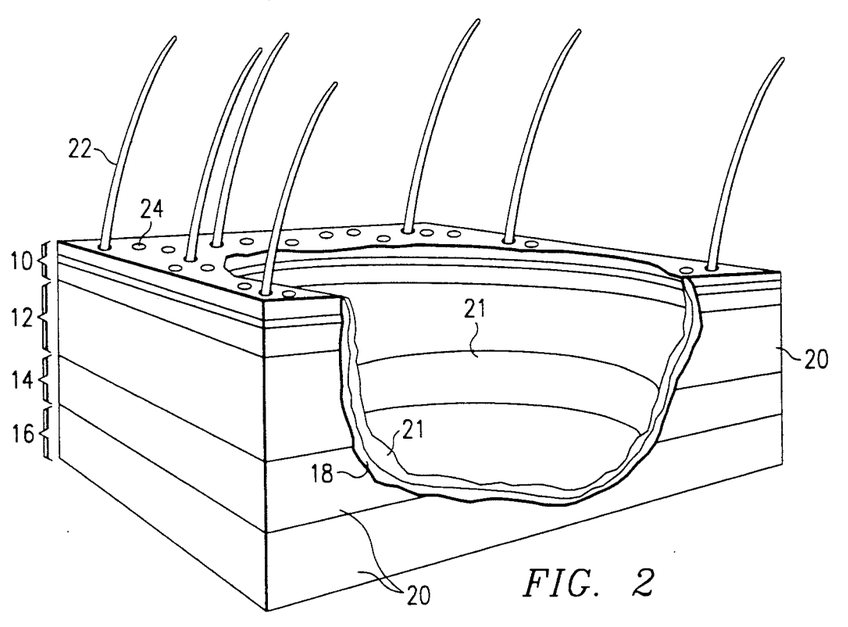
FIG. 2 shows an open wound.

FIG. 2 shows an open wound invading as deep as muscle tissue. The invasive wound invades the epidermis 10, the dermis 12, the subcutaneous fatty tissue 14, and the muscle tissue 16. Hairs 22 and pores 234 are completely absent in this open wound. The wound is surrounded by the dead tissue 21 which is separated from the healthy living tissue 20 by an immune dysfunction zone 18. The purpose of a wound cleanser is to cleanse away any foreign and undesirable materials, including some of the dead tissue, from the wound so that the wound can heal properly.

A wound cleanser of the present invention is suitable for cleansing open wounds such as partial thickness wounds, dehisced wounds, pressure ulcers, venous stasis ulcers, and diabetic ulcers.

Surfactants function to penetrate and wet soiled surfaces, to displace, solubilize, or emulsify various soils, and to disperse or suspend certain soils in solution to prevent their redeposition. A surfactant is an organic compound consisting of two parts: One, a hydrophobic portion, usually including a long hydrocarbon chain; and two, a hydrophilic portion which renders the compound sufficiently soluble or dispersible in water or another polar solvent. The combined hydrophobic and hydrophilic moieties enable the compound to be surface active, thus able to concentrate at the interface between a surfactant solution and another phase, such as soil or other substrate to be cleaned. Surfactants are usually classified into: (1) Anionics, where the hydrophilic moiety of the molecule carries a negative charge; (2) cationics, where this moiety of the molecule carries a positive charge; and (3) nonionics, which do not dissociate, but commonly derive their hydrophilic moiety from polyhydroxy or polyethoxy structures. Other surfactants include ampholytic and zwitterionic surfactants.

Usable nonionic surfactants for this invention include pluronic polyols, polysorbates, sucrose and fatty acid esters. Other examples include sucrose laurate, sucrose oleate and sucrose stearate, and Biolex, sucrose cocoate. A preferred nonionic surfactant is sucrose laurate. Usable ionic surfactants include sodium laureth sulfate and sodium lauryl sulfate.

Unless otherwise defined, the amount of each ingredient or component of the wound cleanser is based on the weight percent of the final aqueous wound cleanser.

The amount of the nonionic surfactant present in the wound cleanser can vary from about 0.01 percent to about 50 percent. Preferably, the amount of the nonionic surfactant present should be in the range of from about 0.1 percent to about 40 percent.

Osmolality is defined as the number of dissolved particles in a unit volume of water solution. Osmolarity is defined as the number of dissolved particles in a unit weight of water solution. As a practical matter, osmolality and osmolarity have numerical values which are very close in the ranges involved in the present invention. A solution that has 1/1000 of an osmol dissolved per kilogram has a concentration of 1 milliosmos per kilogram ("mOs/kg"). A solution that has 1/1000 of an osmol dissolved per liter has a concentration of 1 mOs per liter ("mOs/l"). An osmos is the number of particles in 1 gram molecular weight of undissociated solute. Tonicity is a measure of the osmotic pressure of a solution relative to the osmotic pressure in the blood fluids. It is to be understood that the osmotic pressure of the body varies from one person to another person. A hypotonic solution is a solution of lower osmotic pressure or tonicity than that of blood. The osmolality of a hypotonic solution is usually less than 280 mOs/l. An isotonic solution has the same tonicity as blood. Here, the osmolality usually ranges from about 280 to about 296 mOs/l. A hypertonic solution is a solution of greater than 296 mOs/l. Drinking water normally has an osmolality of less than 20 mOs/l.

The osmolality of the present wound cleanser can vary from about 200 to about 320 mOs/l. Preferably, the osmolality should be n the range of from about 250 to about 310 mOs/l. More preferably, the osmolality should range from about 20 to about 296 mOs/l. Most preferably, the osmolality should range from about 280 to about 285 mOs/l.

The osmotic adjuster of the present invention can be selected from the halide salts, such as those of sodium and potassium; and sugars such as mannitol, glucose, dextrose, and others. Sodium halide salts are preferred over the potassium counterparts. The preferred sugar as an osmotic adjuster is mannitol. The osmotic adjuster should be present in the range of from about 0.05 to about 10 weight percent, based on the total weight of the final wound cleanser. Preferably, the osmotic adjuster should be present in the range of from about 0.1 to about 5 weight percent.

Salts such as sodium and potassium salts of phosphate, borate, and acetate salts of sodium and potassium can be used as a buffering agent to maintain the wound cleanser composition within a desirable pH range. Disodium phosphate is the preferred buffering agent. The buffering agent should be present in the amount in the range of from about 0.05 to about 3 weight percent, based on the total weight of the final wound cleanser, and more preferably in a range of from about 0.1 to about 2 weight percent.

Hydrochloric acid, phosphoric acid, citric acid, sodium hydroxide, and other physiologically compatible acids and bases can all be used to make the necessary adjustment in pH, so that the pH falls within the range of from about 6 to 7.7, or preferably from about 6.8 to about 7.5 and most preferably from about 7.35 to about 7.45.

The present invention can also include a preservative so that the unused portion of the aqueous wound cleanser can pass a preservative challenge test so that this unused portion of the wound cleanser can still be used for cleansing a wound, either the same or a different one, at a later time. Thus, unlike the conventional single-use wound cleanser, the unused portion of which must be discarded, the wound cleanser of the present invention does not require the discarding of the unused portion of the wound cleanser. The "multiple" use versatility of the present invention can thus greatly reduce the medical cost. Examples of preservatives include benzalkonium chloride, methylparaben, potassium sorbate, sodium benzoate, imidazolidinyl urea, thimerosal, and glyceryl monolaurate. Methylparaben is the preferred preservative. The amount of the preservative should be in the range from about 0.001 to about 1 weight percent, based on the total weight of the final wound cleanser. Preferably, the preservative should be present in an amount that ranges from about 0.01 to about 0.4 weight percent.

An optical ingredient that may be used for the present invention is a sudsing agent. A sudsing action can present an aesthetic appeal to the product when in use. Sudsing can be increased by adding small quantities of anionic surfactants, such as mono- and di-ethanol amides of fatty acids having 10-16 carbon atoms. Thus, usable sudsing agents include sodium laureth sulfate and cocoamphodiacetate, with the latter being the preferred one. Sudsing agent employed should be in the range of from about 0.01 to about 5 weight percent, based on the total weight of the final cleanser. Preferably, from about 0.02 to about 3 weight percent of a sudsing agent should be employed. Most preferably, from about 0.05 to about 1 weight percent of a sudsding agent should be employed. Minimal sudsing is preferred.

Another optional ingredient used for the present invention is a skin protectant. Examples of a skin protectant include glycerine, allantoin, zinc acetate, and other water soluble skin protectants. A skin protectant can be present in one embodiment of the invention in the range of from about 0.1 to about 50 weight percent, based on the total weight of the final cleanser. Preferably, from about 0.1 to about 20 weight percent of a skin protectant should be employed. Most preferably, from about 0.5 to about 2 weight percent of a skin protectant should be used.

A stabilizer can also be used in the present invention. A stabilizer will stabilize, and keep in solution, the combination of different ingredients present in the wound cleanser. Examples of stabilizers include salts of ethylenetriaminetetraacetic acid. A sodium salt of the stabilizer is preferred. A stabilizer can be present in the present invention in the range of from about 0.01 to about 3 weight percent, based on the total weight of the final cleanser. Preferably, from about 0.05 to about 2 weight percent of a stabilizer should be employed. Most preferably, from about 0.1 to about 1 weight percent of a stabilizer should be used.

The concentration of the preservative in the stabilizer, and the buffering agent should be minimized yet still provide adequate preservative efficacy and product stability.

EXAMPLE I

A most preferred aqueous wound cleanser was prepared containing the following ingredients:

| Ingredient | Amount (W/W %) |
| --- | --- |
| D.I. Water | 95.35 |
| Sucrose Laurate (Grilloten LSE 65) | 0.50 |
| Methylparaben | 0.10 |
| Disodium EDTA | 0.10 |
| Glyceryl Monolaurate (Lauricidin) | 0.10 |
| Mannitol | 3.60 |
| Cocoamphodiacetate (Velvetex CDC) | 0.05 |
| Disodium Phosphate | 0.20 |

In this case, methylparaben, disodium EDTA, and glyceryl monolaurate add synergistically to provide an efficacious preservative system with minimal toxicity to the wound.

In preparing the above wound cleanser, sucrose laurate (379 g), glyceryl monolaurate (76 g), methylparaben (76 g), disodium EDTA (76 g), and D.I. water (72.18 Kg) were agitated and mixed at a temperature of about 60° C. until all ingredients were essentially in solution. Then the mixture was cooled to about room temperature and mannitol (2.73 Kg) was added with agitation until substantially homogeneous. The whole process took approximately 30 minutes. Then cocoamphodiacetate (37.9 g) and disodium phosphate (151.4 g) were added and mixed with agitation for approximately 30 minutes. The bulk yield of the wound cleanser was about 20 gallons.

EXAMPLE II

The concentrate wound cleanser can be prepared by blending the proper amounts and ratios of all the ingredients together. These ingredients can either be in essentially dry or in concentrated form. Alternatively, the aqueous wound cleanser prepared according to the principles of the present invention can be dehydrated to give the concentrate wound cleanser. This concentrate can later be dissolved in, or constituted with, water to make the final aqueous wound cleanser.

EXAMPLE III

The surface tension of the product obtained from the present invention was determined and compared to other commercially available wound cleansers. Surface tension is widely used to determine the critical micelle concentration (CMC) of nonionic and anionic surfactants commonly present in many wound cleansing products. This information is important for stability of emulsion or suspension formulations. Also, wounds are solid surfaces which may or may not be wetted depending on a surface tension of the liquid. It is well documented that for a liquid to wet the surface of carbon particles, the critical surface energy of the particle must be equal to, or higher than, the surface tension of the liquid.

Surface Tension and Wetting Phenomena

Figure 3:
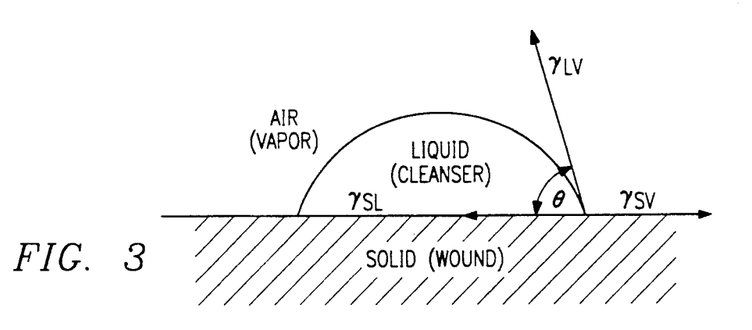
FIG. 3 shows forces acting on liquid drop exhibiting contact angle of $\theta$.

When a liquid does not spread spontaneously over a solid surface, the solid is not wetted. Important parameters which influence the degree of wetting are the angle which the liquid makes with the solid surface at the point of contact and the surface tension of the liquid (FIG. 3). Generally, the contact angle is zero when wetting is complete and greater than zero when not complete, up to a maximum of about 180° for practically no wetting. Contact angle can be expressed in terms of solid-liquid-air equilibrium by Young's equation:

$$YSV = YSL + YLV \cos \theta$$

where YSV, YSL and YLV represent the surface-free energy per unit area of solid-air, solid-liquid and liquid-air interfaces respectively. Factors which tend to reduce YLV (surface tension) and YSL will favor wetting; the greater the value of YSV, the greater the chance for wetting to occur. Theoretically, the lower the surface tension of a liquid, the smaller the contact angle on a given solid. Also, the more polar the solid, the smaller the contact angle with the same liquid, hence improved wetting. Therefore, high energy polar solids such as the surface of wounds will make a smaller contact angle with low surface tension liquids. This, in turn, facilitates wetting and helps to debride wounds.

Experimental

Materials: Sterile 0.9% sodium chloride (Automatic Liquid Packaging Inc., Woodstock, Ill.); Shur-Clens® (Calgon Vestal Labs, St. Louis, Mo.); wound cleanser of the present invention; Biolex Wound Cleanser (Catalina Biochemical Corp., Duarte, Calif.); Dermagran Moisturizing Spray (Dermasciences Inc., Old Forge, Pa.); hydrogen peroxide solution 3% (Hunts Products Co. Inc., Dallas, Tex.); deionized water (Lab R. O. System; Ahlfinger Water Co., Dallas, Tex).

Methods

Each product was mixed thoroughly by shaking and a sample aliquot was placed into acid-washed glass beakers. The sample was allowed to stand for approximately 10 minutes before measurement in order to compensate for any adsorption by the glass beaker. Beakers were then drained and a fresh volume of the same solution was added. The surface tension was measured on a DuNouy tensionmeter as follows: the ring was submerged to about 5 mm below the liquid surface. Measurement was taken after 15 minutes in order to allow molecular orientation equilibrium to take lace.

Results and Discussion

A calibration check on the instrument was performed according to the manufacturer's directions. The recorded dial was approximately 0.4 dynes/cm greater than the calculated value, assuming 980.3 cm/sec$^2$ as the earth's gravity in the Dallas area. Precision and accuracy checks on the tensionmeter were performed by measuring the surface tension of deionized water generated in the laboratory, giving an average surface tension of 73.8±0.5 dynes/cm at 22° C. The calculated apparent surface tension of the wound cleansers are shown below. Results indicate that the wound cleanser composition of the present invention (26.2±0.2 dynes/cm) demonstrated lower surface tension than Shur-Clens® (40.7±0.8 dynes/cm), Biolex wound cleanser (41.3±0.3 dynes/cm), sterile 0.9% sodium chloride (73.4±0.3 dynes/cm) and hydrogen peroxide 3% solution (74.4±0.2 dynes/cm). Shur-Clens® and Biolex are presently widely marketed as wound cleansers. The comparative results are summarized below:

TABLE 1

| Sample Name | Manufacturer | Surface Tension ± S.D. (dynes/cm) |
|---|---|---|
| Wound Cleanser of the Present Invention | Carrington Labs, Inc. | 26.2 ± .2 |
| Shur-Clens ® | Calgon Vestal Labs. | 40.7 ± .8 |
| Biolex Wound Cleanser | Catalina Biomedical | 41.3 ± .3 |
| Dermagran Moisturizing Spray | Dermasciences, Inc. | 59.5 ± .2 |
| Sterile 0.9% Sodium Chloride | Automatic Liquid Packaging, Inc. | 73.4 ± .3 |
| D.I. Water | Laboratory R.O. System | 73.8 ± .5 |
| Hydrogen Peroxide Solution 3% | Medical Center | 74.4 ± .2 |
| Operand Iodine Scrub | General Medical Corp. (Redi Products) | 31.2 ± .5 |
| SAFCLENZ | Calgon Vestal Labs | 47.8 ± .1 |

A practical demonstration revealed that the wound cleanser of the present invention dissolved dried whole blood smeared on microscope slides faster than competitive products. Wound cleansers that failed to dislodge blood from slide mounts had high surface tension readings.

EXAMPLE IV

The wound cleanser formulation prepared according to the principles of the present invention was evaluated in eye irritation rests in rabbits.

Wound cleanser composition of the preset invention, when instilled undiluted into the conjunctival sac of six New Zealand White rabbits and the treated eyes not washed following instillation, produced within one hour, slight watery ocular discharge in three of the animals. The treated eye of each of the three affected animals returned to a reaction-free condition within twenty-four hours following instillation.

A maximum average score of 1.0 was recorded at the one-hour examination interval.

Experimental Procedure

Six healthy young adult New Zealand White rabbits (random sex. Supplier: Doe Valley Farms, Bentonville, Arkansas) were used as subjects to determine the type and extent of ocular reaction resulting from the addition of the test article, wound cleanser composition of the present invention, into the conjunctival sac of the animals.

The animals were individually housed in metal cages suspended above the droppings with feed, consisting of Purina Rabbit Chow, and tap water freely available at all times.

Both eyes of each animal were examined, using 2% Fluorescein Sodium Ophthalmic Solution (Alcon) at twenty-four hours before testing, and only animals without observable eye defects or irritation were used.

One-tenth milliliter of undiluted wound cleanser composition of the present invention was placed in one eye of each animal by gently pulling the lower lid away from the eyeball to form a cup into which the test article was deposited. The lids were then gently held together for one second to ensure complete exposure of the eye. The other eye was not treated and served as a control. The eyes were not washed following instillation.

All animals were immobilized in a suitable restrainer for one hour subsequent to treatment.

The eyes were examined and the grade of ocular reaction was recorded at one and twenty-four hours following exposure using the scale for scoring ocular lesions as outlined by Lehman, A. J. et al., in *Appraisal of the Safety of Chemicals in Foods, Drugs and Cosmetics*, Association of Food and Drug Officials of the United States, Fourth Printing, 1979.

After examination of the eyes of each animal at twenty-four hours, the treated eyes were further examined by placing one drop of Fluorescein Sodium—2% on the cornea. After fifteen seconds, the excess fluorescein was flushed out with sufficient isotonic saline.

Additional observations of the eyes were performed at forty-eight and seventy-two hours following exposure. For both of these intervals, where indicated, Fluorescein Sodium Ophthalmic Solution was used for corneal examination.

NOTE: Fluorescein sodium (2% aq) is used as an ophthalmic diagnostic aid for the detection of corneal lesions.

TABLE 2

Results
Individual Animal Ocular Lesion Data

| Rabbit No. | Structure | 1 Hour | 24 Hours | 48 Hours | 72 Hours |
|---|---|---|---|---|---|
| 1 | Cornea | | | | |
| | Opacity | 0 | 0 | 0 | 0 |
| | Area | 0 | 0 | 0 | 0 |
| | Iris | 0 | 0 | 0 | 0 |
| | Conjunctivae | 0 | | | |
| | Redness | 0 | 0 | 0 | 0 |
| | Chemosis | 0 | 0 | 0 | 0 |
| | Discharge | 0 | 0 | 0 | 0 |
| | Other findings | — | — | — | — |
| 2 | Cornea | | | | |
| | Opacity | 0 | 0 | 0 | 0 |
| | Area | 0 | 0 | 0 | 0 |
| | Iris | 0 | 0 | 0 | 0 |
| | Conjunctivae | | | | |
| | Redness | 0 | 0 | 0 | 0 |
| | Chemosis | 0 | 0 | 0 | 0 |
| | Discharge | 0 | 0 | 0 | 0 |
| | Other findings | — | — | — | — |
| 3 | Cornea | | | | |
| | Opacity | 0 | 0 | 0 | 0 |
| | Area | 0 | 0 | 0 | 0 |
| | Iris | 0 | 0 | 0 | 0 |
| | Conjunctivae | | | | |
| | Redness | 0 | 0 | 0 | 0 |
| | Chemosis | 0 | 0 | 0 | 0 |
| | Discharge | 0 | 0 | 0 | 0 |
| | Other findings | — | — | — | — |
| 4 | Cornea | | | | |
| | Opacity | 0 | 0 | 0 | 0 |
| | Area | 0 | 0 | 0 | 0 |
| | Iris | 0 | 0 | 0 | 0 |
| | Conjunctivae | | | | |
| | Redness | 0 | 0 | 0 | 0 |
| | Chemosis | 0 | 0 | 0 | 0 |
| | Discharge | 0 | 0 | 0 | 0 |
| | Other findings | — | — | — | — |
| 5 | Cornea | | | | |
| | Opacity | 0 | 0 | 0 | 0 |
| | Area | 0 | 0 | 0 | 0 |
| | Iris | 0 | 0 | 0 | 0 |
| | Conjunctivae | | | | |
| | Redness | 0 | 0 | 0 | 0 |
| | Chemosis | 0 | 0 | 0 | 0 |
| | Discharge | 0 | 0 | 0 | 0 |
| | Other findings | — | — | — | — |
| 6 | Cornea | | | | |
| | Opacity | 0 | 0 | 0 | 0 |
| | Area | 0 | 0 | 0 | 0 |
| | Iris | 0 | 0 | 0 | 0 |
| | Conjunctivae | | | | |
| | Redness | 0 | 0 | 0 | 0 |
| | Chemosis | 0 | 0 | 0 | 0 |
| | Discharge | 0 | 0 | 0 | 0 |
| | Other findings | — | — | — | — |

Primary Eye Irritation Scores

A summary of the Draize scores for the 1, 24, 48, and 72-hour observations is given below:

TABLE 3

| Rabbit No. | Structure | 1 Hour | 24 Hours | 48 Hours | 72 Hours |
|---|---|---|---|---|---|
| 1 | Cornea | 0 | 0 | 0 | 0 |
| | Iris | 0 | 0 | 0 | 0 |
| | Conjunctivae | 0 | 0 | 0 | 0 |
| 2 | Cornea | 0 | 0 | 0 | 0 |
| | Iris | 0 | 0 | 0 | 0 |
| | Conjunctivae | 0 | 0 | 0 | 0 |
| 3 | Cornea | 0 | 0 | 0 | 0 |
| | Iris | 0 | 0 | 0 | 0 |
| | Conjunctivae | 0 | 0 | 0 | 0 |
| 4 | Cornea | 0 | 0 | 0 | 0 |
| | Iris | 0 | 0 | 0 | 0 |
| | Conjunctivae | 2 | 0 | 0 | 0 |
| 5 | Cornea | 0 | 0 | 0 | 0 |
| | Iris | 0 | 0 | 0 | 0 |
| | Conjunctivae | 2 | 0 | 0 | 0 |
| 6 | Cornea | 0 | 0 | 0 | 0 |
| | Iris | 0 | 0 | 0 | 0 |
| | Conjunctivae | 2 | 0 | 0 | 0 |
| | Average | 1.0 | 0.0 | 0.0 | 0.0 |

Conclusion

Wound cleanser composition of the present invention, when instilled undiluted into the conjunctival sac of six New Zealand White rabbits and the treated eyes not washed following instillation of the test article, produced within one hour a slight accumulation of watery ocular discharge in three of the animals. The treated eyes of the three remaining animals appeared unremarkable at one hour following instillation.

The treated eye of each of the six animals appeared reaction-free at the twenty-four, forth-eight and seventy-two hour readings.

A maximum average score of 1.0 was recorded at one h our following treatment.

EXAMPLE V

Wound cleanser composition of the present invention was subjected to primary dermal irritation testing in rabbits.

Experimental Procedure

Six healthy young adult New Zealand White rabbits (random sex. Supplier: Doe Valley Farms, Bentonville, Arkansas) were used as subjects to determine the primary irritation/corrosion potentiality of the wound cleanser composition of the present invention when applied topically to the abraded skin of the animals for a period of twenty-four hours. Sterile isotonic saline was tested under similar conditions and served as a control.

he animals were individually housed in metal cages suspended above the droppings, with feed consisting of Purina Rabbit Chow, and tap water freely available at all times.

The backs of the animals were clipped free of hair and the skin examined before testing. Only those animals without ski defects or irritation were used for the study.

Two application sites were selected on each of the animals. The sites were located parallel to each other on opposite sides of the midline of the back. The center area of each of the sites was abraded by making minor incisions through the stratum corneum (not deep enough to disturb the derma).

On the day of the test, the animals were immobilized in a restrainer and 0.5 ml doses of undiluted wound cleanser formulation of the present invention and sterile isotonic saline (0.9% Sodium Chloride Injection, USP, Lot No. C132381; Baxter Healthcare Corp.) were separately applied under one-inch square gauze patches to the prepared application sites on the back of each rabbit. The control saline was applied to the site of each animal designated as the No. 1 site and wound cleanser composition of the present invention was applied to the designated No. 2 sites of the animals. The patches were secured by adhesive tape and the entire trunk of each animal was enclosed in a plastic binder to keep the patches in place and the test and control doses in contact with the skin of their respective treatment sites during the 24-hour exposure period.

Following exposure, the patches were removed and any unabsorbed test or control material was gently washed off the treated areas of skin using lukewarm tap water. The treatment sites were examined and the resulting reactions were separately evaluated for both of the materials using the scoring method of Draize, Woodard and Calvery (As modified by Scientific Associates, Inc.; *J. Pharmacol. Exptl. Therap.*, 82; 377, 1944), as shown below.

TABLE 4

| | Value |
|---|---|
| Erythema and eschar formation: | |
| No erythema | 0 |
| Very slight erythema (barely perceptible) | 1 |
| Well-defined erythema | 2 |
| Moderate to marked erythema | 3 |
| Severe erythema (beet redness) to slight | 4 |
| eschar formation (injuries in depth) | |
| Total possible erythema | 4 |
| Edema formation: | |
| No edema | 0 |
| Very slight edema (barely perceptible, raised less than 1.0 mm) | 1 |
| Slight edema (edges of area well-defined, raised approximately 1.0 mm to less than 2.0 mm) | 2 |
| Moderate to marked edema (raised approximately 2.0 mm to less than 4.0 mm) | 3 |
| Severe edema (raised approximately 4.0 mm, or greater, and/or extending beyond the area of exposure) | 4 |
| Total possible edema score | 4 |

The treated skin was additionally examined and the type and/or grade of dermal reaction recorded at forty-eight and seventy-two hours following test application.

Results

The Draize scores for the control saline and the test article through seventy-two hours post-application are presented as follows:

TABLE 5

| | | Draize Scores | | |
|---|---|---|---|---|
| Rabbit No. | Reaction | 24 Hrs | 48 Hrs | 72 Hrs |
| No. 1 Sites - Control: 0.9% Sodium Chloride Injection USP | | | | |
| 1 | Erythema and Eschar | 0 | 0 | 0 |
| | Edema Formation | 0 | 0 | 0 |
| 2 | Erythema and Eschar | 0 | 0 | 0 |
| | Edema Formation | 0 | 0 | 0 |
| 3 | Erythema and Eschar | 0 | 0 | 0 |
| | Edema Formation | 0 | 0 | 0 |
| 4 | Erythema and Eschar | 0 | 0 | 0 |
| | Edema Formation | 0 | 0 | 0 |
| 5 | Erythema and Eschar | 0 | 0 | 0 |
| | Edema Formation | 0 | 0 | 0 |
| 6 | Erythema and Eschar | 0 | 0 | 0 |
| | Edema Formation | 0 | 0 | 0 |
| Erythema and Eschar Average Value | | 0.0 | 0.0 | 0.0 |
| Edema Formation Average Value | | 0.0 | 0.0 | 0.0 |

0.9% Sodium Chloride Injection, USP, when applied undiluted for twenty-four hours to the abraded sin of six New Zealand White rabbits, was found to produce no grossly discernible signs of a dermal reaction during the study period.

TABLE 6

| | | Draize Scores | | |
|---|---|---|---|---|
| Rabbit No. | Reaction | 24 Hrs | 48 Hrs | 72 Hrs |
| No. 2 Sites - Test: Wound Cleanser of the Present Invention | | | | |
| 1 | Erythema and Eschar | 0 | 0 | 0 |
| | Edema Formation | 0 | 0 | 0 |
| 2 | Erythema and Eschar | 0 | 0 | 0 |
| | Edema Formation | 0 | 0 | 0 |
| 3 | Erythema and Eschar | 0 | 0 | 0 |
| | Edema Formation | 0 | 0 | 0 |
| 4 | Erythema and Eschar | 0 | 0 | 0 |
| | Edema Formation | 0 | 0 | 0 |
| 5 | Erythema and Eschar | 0 | 0 | 0 |
| | Edema Formation | 0 | 0 | 0 |
| 6 | Erythema and Eschar | 0 | 0 | 0 |
| | Edema Formation | 0 | 0 | 0 |
| Erythema and Eschar Average Value | | 0.0 | 0.0 | 0.0 |

TABLE 6-continued

| Rabbit No. Reaction | Draize Scores | | |
|---|---|---|---|
| | 24 Hrs | 48 Hrs | 72 Hrs |
| Edema Formation Average Value | 0.0 | 0.0 | 0.0 |

Wound cleanser composition of the present invention, when applied undiluted for twenty-four hours to the abraded skin of six New Zealand White rabbits, was found to produce no grossly discernible signs of a dermal reaction during the study period. Sterile saline, used as a control, was likewise found to produce a negative dermal reaction.

EXAMPLE VI

For comparison purposes, physical properties of different wound cleansers were summarized in the following table.

TABLE 7

COMPARISON OF SOME COMMERCIALLY AVAILABLE WOUND CLEANSERS

| CHARACTERISTICS | WOUND CLEANSER OF THE PRESENT INVENTION 00710 | CARRINGTON'S CARA-KLENZ 103191 | SHUR-CLENS A9L 126 | BIOLEX WOUND CLEANSER LH13B | DERMA-GRAM MOISTURE SPRAY 13493 |
|---|---|---|---|---|---|
| PHYSIOLOGICAL pH (7.2-7.4) | YES | NO | YES | NO | NO |
| | 7.37 ± .01 | 5.62 ± .01 | 7.26 ± .01 | 5.40 ± .01 | 4.15 ± .00 |
| PHYSIOLOGICAL OSMOLALITY (280-296 mOsm) | YES | NO | NO | NO | NO |
| | 296 ± 1 | 107 ± 1 | **2821 ± 2 | 168 ± 0 | 1452 ± 2 |
| PASSES PRESERVATIVE CHALLENGE* | YES | YES | SINGLE USE NOT ANTIMICROBIAL | YES | — |
| DECREASED SURFACE TENSION | STRONG | STRONG | MEDIUM | MEDIUM | MEDIUM |
| STRONG = ≦35 dynes/cm MEDIUM = 35-60 dynes/cm WEAK = ≧60 dynes/cm | 26.2 ± .2 | 33.6 ± .2 | 40.7 ± .8 | 41.3 ± .3 | 59.5 ± .2 |
| PASSES DRAIZE EYE TEST | YES | YES | YES | YES | — |
| PASSES DERMAL SENSITIVITY TEST | YES | YES | YES | YES | — |

| CHARACTERISTICS | STERILE 0.9% SODIUM CHLORIDE OJ509 | D.I. WATER | HYDROGEN PEROXIDE SOLUTION 3% 0045BD2 | OPERAND IODINE SCRUB 35886A | SAF CLENZ 14MO |
|---|---|---|---|---|---|
| PHYSIOLOGICAL pH (7.2-7.4) | NO | NO | NO | NO | NO |
| | 5.74 ± .02 | 6.03 ± .04 | 4.20 ± .00 | 3.40 ± .02 | 6.44 ± .01 |
| PHYSIOLOGICAL OSMOLALITY (280-296 mOsm) | YES | NO | NO | NO | NO |
| | 285 ± 0 | 0 ± 0 | 908 ± 1 | **2967 ± 2 | 327 ± 1 |
| PASSES PRESERVATIVE CHALLENGE* | NO | NO | YES | YES | — |
| DECREASED SURFACE TENSION | WEAK | WEAK | WEAK | STRONG | MEDIUM |
| STRONG = ≦35 dynes/cm MEDIUM = 35-60 dynes/cm WEAK = ≧60 dynes/cm | 73.4 ± .3 | 73.8 ± .5 | 74.4 ± .2 | 31.2 ± .5 | 47.8 ± .1 |
| PASSES DRAIZE EYE TEST | YES | — | NO | NO | YES |
| PASSES DERMAL SENSITIVITY TEST | YES | — | — | — | YES |

*CHALLENGED WITH S. aureus, E. Coli, S. Typhimurium, Ps. aeruginosa, C. albicans, A. niger, B. subtilis, Ps. cepacia It is clear that the present invention is well adapted to carry out the objects and attain the ends and advantages mentioned herein as well as those inherent in the invention. While presently preferred embodiments of the invention have been described for purposes of this disclosure, numerous changes ay be made which will readily suggest themselves to those skilled in the art and which are accomplished within the spirit of the invention disclosed and as defined in the appended claims.

What is claimed is:

1. A physiologically compatible aqueous wound cleanser composition which passes both Draize eye irritation test and primary dermal irritation test, said composition comprising, on a weight percent basis:

from about 0.01 to about 50 percent of a surfactant to give said composition a surface tension of below about 30 dynes/cm;

from about 0.05 to about 10 percent of an osmotic adjuster to give said composition an osmolality of from about 200 to about 320 mOs/liter;

from about 0.05 percent to about 3 percent of a buffering agent to maintain a pH in a range of from about 6 to about 7.7 in said composition; and a sufficient amount of water necessary to establish the foregoing properties.

2. A physiologically compatible aqueous wound cleanser according to claim 1 further comprising from about 0.001 to about 1 percent of a preservative.

3. A physiologically compatible aqueous wound cleanser according to claim 2 wherein said preservative is selected from the group consisting of potassium sorbate, sodium benzoate, benzalkonium chloride, imidazolidinyl urea, glyceryl monolaurate, and thimerosal.

4. A physiologically compatible aqueous wound cleanser according to claim 2 wherein said preservative is methylparaben.

5. A physiologically compatible aqueous wound cleanser according to claim 1 further comprising from about 0.01 to about 5 percent of a sudsing agent.

6. A physiologically compatible aqueous wound cleanser according to claim 5 wherein said sudsing agent is selected for the group consisting of sodium laureth sulfate and cocoamphodiacetate.

7. A physiologically compatible aqueous wound cleanser according to claim 1 further comprising from about 0.1 to about 50 percent of a skin protectant.

8. A physiologically compatible aqueous wound cleanser according to claim 7 wherein aid skin protectant is selected from the group consisting of glycerine, allantoin and zinc acetate.

9. A physiologically compatible aqueous wound cleanser according to claim 1 further comprising a pH adjuster.

10. A physiologically compatible aqueous wound cleanser according to claim 9 wherein said pH adjuster is selected from the group consisting of hydrochloric acid, citric acid, phosphoric acid, and sodium hydroxide.

11. A physiologically compatible aqueous wound cleanser according to claim 1 further comprising from about 0.01 to about 3 percent of a stabilizer.

12. A physiologically compatible aqueous wound cleanser according to claim 11 wherein said stabilizer is a sodium salt of ethylenetriaminetetraacetic acid.

13. A physiologically compatible aqueous wound cleanser according to claim 1 wherein said surfactant is a nonionic surfactant.

14. A physiologically compatible aqueous wound cleanser according to claim 1 wherein said surfactant is selected from the group consisting of sucrose laurate, sucrose oleate, sucrose stearate, and sodium lauryl sulfate.

15. A physiologically compatible aqueous wound cleanser according to claim 1 wherein said osmotic adjuster is selected from the group consisting of mannitol, glucose, and dextrose.

16. A physiologically compatible aqueous wound cleanser according to claim 1 wherein said buffering agent is selected from the group consisting of sodium salts of phosphate, borate, and acetate.

17. A physiologically compatible aqueous wound cleanser composition comprising, on a weight percent basis:
   from about 0.01 to about 40 percent of a surfactant t give said composition a surface tension of below about 30 dynes/cm;
   from about 0.01 to about 5 percent of an osmotic adjuster to give said composition an osmolality of from about 250 to about 310 mOs/liter;
   from about 0.01 to about 2 percent of a buffering agent to maintain a pH in a range of from about 6.8 to about 7.5 in said composition; and
   a sufficient amount of water necessary to establish the foregoing properties.

18. A physiologically compatible aqueous wound cleanser according to claim 17 further comprising from about 0.01 to about 0.4 percent of a preservative.

19. A physiologically compatible aqueous wound cleanser according to claim 18 wherein said preservative is selected from the group consisting of potassium sorbate, sodium benzoate, benzalkonium chloride, imidazolidinyl urea, glyceryl monolaurate, and thimerosal.

20. A physiologically compatible aqueous wound cleanser according to claim 18 wherein said preservative is methylparaben.

21. A physiologically compatible aqueous wound cleanser according to claim 17 further comprising from about 0.02 to about 3 percent of a sudsing agent.

22. A physiologically compatible aqueous wound cleanser according to claim 21 wherein said sudsing agent is selected for the group consisting of sodium laureth sulfate and cocoamphodiacetate.

23. A physiologically compatible aqueous wound cleanser according to claim 17 further comprising from about 0.1 to about 20 percent of a skin protectant.

24. A physiologically compatible aqueous wound cleanser according to claim 23 wherein said skin protectant is selected from the group consisting of glycerine, allantoin and zinc acetate.

25. A physiologically compatible aqueous wound cleanser according to claim 17 further comprising a pH adjuster.

26. A physiologically compatible aqueous wound cleanser according to claim 25 wherein said pH adjuster is selected from the group consisting of hydrochloric acid, citric acid, phosphoric acid, and sodium hydroxide.

27. A physiologically compatible aqueous wound cleanser according to claim 17 further comprising from about 0.05 to about 2 percent of a stabilizer.

28. A physiologically compatible aqueous wound cleanser according to claim 27 wherein said stabilizer is a sodium salt of ethylenetriaminetetraacetic acid.

29. A physiologically compatible aqueous wound cleanser according to claim 17 wherein said surfactant is a nonionic surfactant.

30. A physiologically compatible aqueous wound cleanser according to claim 29 wherein said surfactant is selected from the group consisting of sucrose laurate, sucrose oleate, sucrose stearate, and sodium lauryl sulfate.

31. A physiologically compatible aqueous wound cleanser according to claim 17 wherein said osmotic adjuster is selected from the group consisting of mannitol, glucose, and dextrose.

32. A physiologically compatible aqueous wound cleanser according to claim 17 wherein said buffering agent is selected from the group consisting of sodium salts of phosphate, borate, and acetate.

33. A physiologically compatible aqueous wound cleanser composition which passes both Draize eye irritation test and primary dermal irritation test, said composition comprising, on a weight percent basis:
   from about 0.25 to about 0.75 percent of a sucrose laurate;
   from about 0.05 to about 0.15 percent of methylparaben;
   from about 0.05 to about 0.15 percent of disodium EDTA;
   from about 0.05 to about 0.15 percent of glyceryl monolaurate;
   from about 2 to about 5 percent of mannitol;
   from about 0.02 to about 0.08 percent of cocoamphodiacetate;
   from about 0.1 to about 0.3 percent of disodium phosphate; and
   a sufficient amount of water, such that said aqueous wound cleanser composition is characterized as having a surface tension of below about 30 dynes/cm, an osmolality of from about 280 jto about 296 mOs/liter, and a pH in the range of from about 7.35 to about 7.45.

34. A concentrated dry mixture suitable for reconstituting with water to form a final aqueous wound cleanser that is physiologically compatible and which passes both Draize eye irritation test and primary dermal irritation test, said essentially dry mixture comprising:
- a surfactant;
- an osmotic adjuster; and
- a buffering agent, such that when said concentrated mixture is reconstituted with said water to give said final aqueous wound cleanser, said final aqueous wound cleanser has, on a weight percent basis, from about 0.01 to about 50 percent of said surfactant, from about 0.05 to about 10 percent of said osmotic adjuster and from about 0.05 to about 3 percent of said buffering agent, and said final aqueous wound cleanser is further characterized as having a surface tension of below about 30dynes/cm, an osmolality of from about 200 to about 320 mOs/liter, and a pH in the range of from about 6 to about 7.7.

35. A concentrated mixture according to claim 34 further comprising a sufficient amount of a preservative, such that when said concentrated mixture is reconstituted with said water, said final aqueous wound cleanser has a concentration of from about 0.001 to about 1 percent of said preservative.

36. A concentrated mixture according to claim 35 wherein said preservative is selected from the group consisting of potassium sorbate, sodium benzoate, imidazolidinyl urea, glyceryl monolaurate, thimerosal, and benzalkonium chloride.

37. A concentrated mixture according to claim 35 wherein said preservative is methylparaben.

38. A concentrated mixture according to claim 34 further comprising a sufficient amount of a sudsing agent, such that when said concentrated mixture is reconstituted with said water, said final aqueous wound cleanser has a concentration of from about 0.01 to about 5 percent of said sudsing agent.

39. A concentrated mixture according to claim 38 wherein said sudsing agent is selected from the group consisting of sodium laureth sulfate and cocoamphodiacetate.

40. A concentrated mixture according to claim 34 further comprising a sufficient amount of a protectant, such that when said concentrated mixture is reconstituted with said water, said final aqueous wound cleanser has a concentration of from about 0.1 to about 50 percent of said protectant.

41. A concentrated mixture according to claim 40 wherein said skin protectant is selected from the group consisting of glycerine, allantoin and zinc acetate.

42. A concentrated mixture according to claim 34 further comprising a pH adjuster.

43. A concentrated mixture according to claim 42 wherein said pH adjuster is selected from a group consisting of hydrochloric acid, citric acid, phosphoric acid, and sodium hydroxide.

44. A concentrated mixture according to claim 34 further comprising a sufficient amount of a stabilizer, such that when said concentrated mixture is reconstituted with said water, said final aqueous wound cleanser has a concentration of from about 0.01 to about 3 percent of said stabilizer.

45. A concentrated mixture according to claim 44 wherein said stabilizer is a sodium salt of ethylenetriaminetetraacetic acid.

46. A concentrated mixture according to claim 34 wherein said surfactant is a nonionic surfactant.

47. A concentrated mixture according to claim 46 wherein said surfactant is selected from the group consisting of sucrose laurate, sucrose, oleate, sucrose stearate, and sodium lauryl sulfate.

48. A concentrated mixture according to claim 34 wherein said osmotic adjuster is selected from the group consisting of mannitol, glucose, and dextrose.

49. A concentrated mixture according to claim 34 wherein said buffering agent is selected from the group consisting of sodium salts of phosphate, borate, and acetate.

50. A concentrated mixture according to claim 34 wherein said concentrated mixture is essentially dry.

* * * * *

UNITED STATES PATENT AND TRADEMARK OFFICE
CERTIFICATE OF CORRECTION

PATENT NO. : 5,284,833
DATED : February 8, 1994
INVENTOR(S) : Bill H. McAnalley, et al.

It is certified that error appears in the above-indentified patent and that said Letters Patent is hereby corrected as shown below:

Column 1, line 31, [page 2, line 12], "circulation" should be --circulating--.

Column 1, line 56 [page 3, line 10], "firs" should be --first--.

Column 2, line 3 [page 3, line 22], "would" should be --wound--.

Column 2, line 4 [page 3, line 23], "would" should be --wound--.

Column 2, line 13 [page 4, line 7], "would" should be --wound--.

Column 2, line 25 [page 4, line 17], "would" should be --wound--.

Column 3, line 16 [page 6, line 20] "issue" should be --tissue--.

Column 3, line 35 [page 7, line 12] "()" should be --(--.

Column 3, line 38 [page 7, line 14] "polyoxamer" should be --poloxamer--.

Column 3, line 57 [page 7, line 7] "sin" should be --skin--.

Column 3, line 62 [page 7, line 10] ";" should be --:--.

Column 4, line 24 [page 9, line 11] "from" should be --form--.

Column 4, line 29 [page 9, line 16] "o" should be --to--.

UNITED STATES PATENT AND TRADEMARK OFFICE
CERTIFICATE OF CORRECTION

PATENT NO. : 5,284,833
DATED : February 8, 1994
INVENTOR(S) : Bill H. McAnalley, et al.

It is certified that error appears in the above-indentified patent and that said Letters Patent is hereby corrected as shown below:

Column 4, line 30 [page 9, line 17] "ut" should be --but--.

Column 5, line 5 [page 11, line 6] "230" should be --320--.

Column 6, line 9 [page 13, line 18] "234" should be --24--.

Column 7, line 14 [page 16, line 8] "n" should be --in--.

Column 7, line 16 [page 16, line 9] "20" should be --280--.

Column 8, line 1 [page 18, line 5] "optical" should be --optional--.

Column 9, line 63 [page 22, line 14] "Ill." should be --IL.--.

Column 10, line 1 [page 22, line 20] "Tex." should be --TX--.

Column 10, line 63 [page 24, line 27] "rests" should be --tests--.

Column 10, line 64 [page 24, line 28] "preset" should be --present--.

Column 11, line 58 [page 27, line 9] "Iris" should be --*Iris*--.

Column 11, line 59 [page 27, line 10] please delete "0" after the word "*Conjunctivae*".

Column 11, line 63 [page 27, line 14] "Other findings" should be --*Other findings*--.

UNITED STATES PATENT AND TRADEMARK OFFICE
CERTIFICATE OF CORRECTION

PATENT NO. : 5,284,833

DATED : February 8, 1994

INVENTOR(S) : Bill H. McAnalley, et al.

It is certified that error appears in the above-indentified patent and that said Letters Patent is hereby corrected as shown below:

Column 11, line 67 [page 27, line 19] "Iris" should be --<u>Iris</u>--.

Column 12, line 8 [page 27, line 24] "Other findings" should be --<u>Other findings</u>--.

Column 12, line 12 [page 27, line 29] "Iris" should be --<u>Iris</u>--.

Column 12, line 16 [page 27, line 34] "Other findings" should be --<u>Other findings</u>--.

Column 12, line 19 [page 28, line 8] "Iris" should be --<u>Iris</u>--.

Column 12, line 23 [page 28, line 13] "Other findings" should be --<u>Other findings</u>--.

Column 12, line 27 [page 28, line 18] "Iris" should be --<u>Iris</u>--.

Column 12, line 31 [page 28, line 23] "Other findings" should be --<u>Other findings</u>--.

Column 12, line 35 [page 28, line 28] "Iris" should be --<u>Iris</u>--.

Column 12, line 39 [page 28, line 33] "Other findings" should be --<u>Other findings</u>--.

Column 12, line 42 [page 29, line 1] "Primary Eye Irritation Scores" should be --<u>Primary Eye Irritation Scores</u>--.

Column 12, line 66 [page 29, line 26] "Conclusion" should be --<u>Conclusion</u>:--.

Column 13, line 8 [page 30, line 4] "forth" should be --forty--.

UNITED STATES PATENT AND TRADEMARK OFFICE
CERTIFICATE OF CORRECTION

PATENT NO. : 5,284,833
DATED : February 8, 1994
INVENTOR(S) : Bill H. McAnalley, et al.

It is certified that error appears in the above-indentified patent and that said Letters Patent is hereby corrected as shown below:

Column 13, line 18 [page 30, line 11] "Experimental Procedure" should be --Experimental Procedure:--.

Column 13, line 28 [page 30, line 20] "he" should be --The--.

Column 13, line 34 [page 30, line 24] "ski" should be --skin--.

Column 13, line 67 [page 32, line 1] "82;" should be --82:--.

Column 14, line 25 [page 33, line 1] "Results" should be --Results:--.

Column 14, line 49 [page 33, line 24] "sin" should be --skin--.

Column 15, line 62 [page 36, line 5] "ay" should be --may--.

Column 17, line 7 [page 38, claim 8] after the word "wherein" delete the word "aid" and insert the word --said--.

Column 17, line 43 [amended claim 17-Amendment Under 37 C.F.R. Section 1.111 dated 6/3/93], after the word "surfactant" delete the letter "t" and insert the word --to--.

UNITED STATES PATENT AND TRADEMARK OFFICE
CERTIFICATE OF CORRECTION

PATENT NO. : 5,284,833

DATED : February 8, 1994

INVENTOR(S) : Bill H. McAnalley, et al.

It is certified that error appears in the above-indentified patent and that said Letters Patent is hereby corrected as shown below:

Column 18, line 62 [amended claim 33-Amendment Under 37 C.F.R. Section 1.111 dated 6/3/93], "jto" should be --to--.

Signed and Sealed this

Twenty-fourth Day of January, 1995

Attest:

BRUCE LEHMAN

Attesting Officer      Commissioner of Patents and Trademarks